United States Patent
Carlessi et al.

(10) Patent No.: US 9,199,926 B2
(45) Date of Patent: Dec. 1, 2015

(54) PROCESS FOR THE SYNTHESIS OF UREA COMPRISING A PASSIVATION STREAM AT THE STRIPPER BOTTOM

(71) Applicant: SAIPEM S.p.A., San Donato Milanese (IT)

(72) Inventors: Lino Carlessi, Bergamo (IT); Alessandro Gianazza, Milan (IT)

(73) Assignee: SAIPEM S.p.A., San Donato Milanese (IT)

( * ) Notice: Subject to any disclaimer, the term of this patent is extended or adjusted under 35 U.S.C. 154(b) by 0 days.

(21) Appl. No.: 14/371,144

(22) PCT Filed: Jan. 9, 2013

(86) PCT No.: PCT/EP2013/050247
§ 371 (c)(1),
(2) Date: Jul. 8, 2014

(87) PCT Pub. No.: WO2013/104638
PCT Pub. Date: Jul. 18, 2013

(65) Prior Publication Data
US 2015/0025273 A1    Jan. 22, 2015

(30) Foreign Application Priority Data

Jan. 9, 2012  (IT) ............... MI2012A0013

(51) Int. Cl.
*C07C 273/04* (2006.01)
*B01D 3/00* (2006.01)

(52) U.S. Cl.
CPC .............. *C07C 273/04* (2013.01); *B01D 3/009* (2013.01)

(58) Field of Classification Search
CPC .............................. C07C 273/04; B01D 3/009
See application file for complete search history.

(56) References Cited

U.S. PATENT DOCUMENTS

| | | | |
|---|---|---|---|
| 3,984,469 A | 10/1976 | Guadalupi et al. | |
| 4,092,358 A | 5/1978 | Guadalupi et al. | |
| 4,137,262 A | 1/1979 | Guadalupi et al. | |
| 4,208,347 A | 6/1980 | Pagani | |
| 4,314,077 A | 2/1982 | Zardi et al. | |
| 4,354,040 A | 10/1982 | Inoue et al. | |
| 4,801,745 A | 1/1989 | Meessen et al. | |
| 5,597,454 A * | 1/1997 | Lee ................................ | 203/49 |
| 5,886,222 A * | 3/1999 | Rescalli ........................ | 564/70 |
| 6,150,555 A | 11/2000 | Pagani et al. | |
| 8,106,241 B2 * | 1/2012 | Carlessi et al. ................ | 564/70 |
| 8,927,770 B2 * | 1/2015 | Carlessi et al. ................ | 564/71 |

FOREIGN PATENT DOCUMENTS

| | | |
|---|---|---|
| CN | 1376668 | 10/2002 |
| CN | 1463964 | 12/2003 |
| CN | 101679224 | 3/2010 |
| DE | 2116267 | 10/1971 |
| EP | 0306614 | 3/1989 |
| FR | 2489323 | 3/1982 |
| GB | 1184004 | 3/1970 |
| GB | 1292515 | 10/1972 |
| WO | WO 2008/141832 | 11/2008 |

OTHER PUBLICATIONS

International Search Report and Written Opinion for International Application No. PCT/EP2013/050247 dated Mar. 7, 2013.
Notification Concerning Submission, Obtention or Transmittal of Priority Document (Form PCT/IB/304) for International Application No. PCT/EP2013/050247 dated Mar. 15, 2013.

* cited by examiner

*Primary Examiner* — Sudhakar Katakam
(74) *Attorney, Agent, or Firm* — Neal, Gerber & Eisenberg LLP (57) ABSTRACT

A process for the direct synthesis of urea from ammonia and carbon dioxide with increased corrosion resistance, comprising, in the high-pressure synthesis section, a reaction step in a vertical reactor fed with at least one stream of fresh carbon dioxide containing a passivating agent and a decomposition-stripping step of the non-converted reagents, wherein the gas-liquid mixture collected at the head of the reactor is separated into a gaseous stream and a liquid stream fed to the tail and head of the stripper, respectively.

15 Claims, 1 Drawing Sheet

PROCESS FOR THE SYNTHESIS OF UREA COMPRISING A PASSIVATION STREAM AT THE STRIPPER BOTTOM

PRIORITY CLAIM

This application is a national stage application of PCT/EP2013/050247, filed on Jan. 9, 2013, which claims the benefit of and priority to Italian Patent Application No. MI2012A 000013, filed on Jan. 9, 2012, the entire contents of which are each incorporated by reference herein.

BACKGROUND

Various processes are currently known in the state of the art, for the production of urea.

In particular, the synthesis of urea is effected by reacting ammonia and carbon dioxide at a high pressure and temperature, followed by separation of the urea from the mixture containing the non-reacted products and recycling of the same to the reactor.

All industrial processes for the preparation of urea are therefore based on direct synthesis according to the following reaction:

$$2NH_3 + CO_2 \leftrightarrow CO(NH_2)_2 + H_2O \quad (1)$$

This synthesis is carried out in two different reaction steps:

$$NH_3 + CO_2 \leftrightarrow (NH_2)COONH_4 \quad (1a)$$

$$(NH_2)COONH_4 \leftrightarrow CO(NH_2)_2 + H_2O \quad (1b)$$

In the first step (1a), an exothermic equilibrium reaction takes place, having a high reaction rate at room temperature, which, however, at the high temperatures necessary for step (1b), requires high pressures in order to reach a favourable equilibrium.

In the second step (1b), an endothermic reaction takes place, which only reaches a significant rate at high temperatures (>150° C.) with a state of equilibrium which at 185° C., starting from a mixture of reagents in a stoichiometric ratio, leads to a $CO_2$ conversion of slightly over 50%. This unsatisfactory conversion can be conveniently increased by raising the $NH_3/CO_2$ ratio.

The above-mentioned two reaction steps do not normally take place in separate areas of the reactor, but contemporaneously in the reaction mixture, said mixture therefore comprising urea, water, ammonia, carbon dioxide and ammonium carbamate, with a relative concentration, in different areas of the reactor, depending on the various thermodynamic and kinetic factors that contribute to the process.

Processes for obtaining urea by direct synthesis starting from ammonia and carbon dioxide have been widely described in specific literature in the field. An extensive review of the most common processes for the production of urea can be found, for example, in the publication "Encyclopaedia of Chemical Technology" Ed. Kirk-Othmer, Wiley Interscience, third ed. (1983), vol. 23, pages 548-575.

Industrial processes for the production of urea, normally carry out the synthesis in a reactor fed with $NH_3$, $CO_2$ and aqueous solutions of ammonium carbonate and/or carbamate coming from the recycled streams of non-converted reagents, at temperatures ranging from 150 to 215° C., at pressures of at least 13.2 MPa (130 atm), with a $NH_3/CO_2$ molar ratio ranging from 2.5 to 5, calculated with respect to the sum of the feeding streams, including ammonia and $CO_2$ in the form of ammonium carbamate/carbonate. In addition to the water formed and excess of $NH_3$ fed, the reactor effluent still has considerable amounts of $CO_2$, mainly in the form of non-converted ammonium carbamate.

A further essential aspect for obtaining an optimal conversion is also the control of the thermal level in the reactor, as both excessively high and also excessively low temperatures lead to a reduction in the conversion due to the competition of various chemical and thermodynamic factors.

The separation of urea from the water and non-converted reagents is effected in several sections operating at decreasing temperatures and pressures, in which the decomposition of ammonium carbamate to $NH_3$ and $CO_2$ is effected, which are then available for recycling to the reactor. The section for the separation and recycling of the carbamate has investment costs which heavily influence the cost of the final product.

Known processes which operate according to the above general scheme are, for example, described in U.S. Pat. No. 4,092,358; U.S. Pat. No. 4,208,347; U.S. Pat. No. 4,801,745 and U.S. Pat. No. 4,354,040.

In particular, the urea contained in the aqueous solution leaving the reactor is separated from most of the non-transformed ammonium carbamate and excess ammonia used in the synthesis, in a suitable decomposer-evaporator (hereinafter called "stripper", which is the term normally used in the field) operating at pressures the same or slightly lower than the synthesis pressure.

The decomposition of the ammonium carbamate is effected in the stripper providing heat from the outside using indirect thermal exchange with a warmer fluid, normally vapour at 1.8-3.0 MPa, possibly stripping the decomposition products with inert gases or ammonia or carbon dioxide or mixtures of inert gases with ammonia and/or carbon dioxide, the stripping possibly also being effected by exploiting the excess ammonia dissolved in the urea solution (self-stripping), and consequently without having to feed the stripping agent separately.

The decomposition products of the carbamate, together with the possible stripping agents, with the exception of the inert products, are normally condensed in condensers, obtaining a liquid which is recycled to the synthesis reactors.

Further documents that can be mentioned for reference purposes are U.S. Pat. No. 4,314,077; Great Britain Patent No. 1,184,004; Great Britain Patent No. 1,292,515; U.S. Pat. No. 3,984,469; U.S. Pat. No. 4,137,262; German Patent No. 2,116,267 and French Patent No. 2,489323, all describing processes for the production of urea with the above-mentioned characteristics.

Particularly delicate steps in the synthesis process of urea are those in which the ammonium carbamate is present at the highest concentration and temperature, and consequently in the processes mentioned above, these steps coincide with the decomposition-stripping and condensation steps of ammonium carbamate.

One of the problems to be solved in these steps is the corrosion of the equipment used, caused by the extremely aggressive characteristics that take place inside the same, due to both the presence of a high concentration of saline solutions and also as a result of mechanical stress phenomena of the surfaces in the decomposition and release areas of the gaseous phase.

In order to overcome certain of these drawbacks, certain of the known art suggests, for example, the use of special materials in producing the stripper, in particular Ti, Zr, special urea-grade stainless steels, or combinations of the same. Again according to the state of the art, it is advantageous to feed a certain quantity of air or other passivating agent, in order to prolong the corrosion resistance of the materials, especially stainless steels, favouring the formation of a stable layer of oxide on the surfaces exposed to contact with the process fluids.

At present, in this type of plant, in order to effect the passivation of the stripper (especially if the surfaces exposed to corrosion are made of titanium or stainless steel) a certain quantity of air is added at the bottom of the stripper. This addition is effected using a specific injection of air using compressors explicitly prepared for this purpose. In the other parts of the high-pressure urea synthesis loop which require passivation, this passivation is effected, on the contrary, again with air, which is mixed during the suction phase of the $CO_2$ compressor and is sent through the compressor to the urea reactor. The air which has not participated in the passivation reaction in the reactor, leaves the reactor together with the reaction mixture and is sent to the upper part of the stripper, then passing to the carbamate condenser and from here to the carbamate separator, thus leaving the synthesis loop through the valve destined for the pressure control of the loop itself, normally also used for purging the inert products.

During this way, the air effects the passivation of the surfaces of the equipment the air encounters, which would otherwise be subjected to corrosive processes.

In consideration of what is specified above (i.e., the fact that the passivation air is sent from the reactor to the upper part of the stripper), the bottom of the stripper is excluded from the passivation action exerted by said air, which is mixed during the suction phase of the $CO_2$ compressor and sent to the reactor through the compressor.

For this reason, certain of the known art describes the necessity of effecting a specific injection of air at the stripper bottom using compressors explicitly prepared for this purpose.

This solution, however, requires further dedicated devices (i.e., compressors), which, in addition to having a cost, also require periodic maintenance interventions.

Alternative procedures have been proposed for the feeding of a passivating agent (particularly air or oxygen at low concentrations), tending to avoid the use of further high-pressure pumping mechanisms, such as, for example, the scheme described in PCT Patent Application No. WO08/141832, in which a part of fresh carbon dioxide containing passivation air is fed, after compression, to the bottom of the stripper, where it exerts a passivating action on the surfaces most exposed to corrosion.

Although this expedient avoids resorting to the separate pumping of the passivation air, this expedient however requires a careful control of the process conditions in the synthesis cycle with self-stripping based on $NH_3$, due to the reduced amount of $CO_2$ sent to the reactor.

BRIEF DESCRIPTION OF THE DRAWINGS

A non-limiting embodiment of the present disclosure will be described by way of example with reference to the accompanying drawings, in which.

DETAILED DESCRIPTION

The present disclosure relates to an enhanced process for the synthesis of urea, comprising a passivation stream at the bottom of the stripper. That is, a process has now been found by the Applicant which overcomes certain of the above drawbacks, specifically of the state of the art, at the same time further optimizing the synthesis process of urea.

In particular, the present disclosure falls within the specific field of plants for the synthesis of urea with stripping using ammonia (i.e., in plants in which the stripping action in the stripper), in which the decomposition of the carbamate takes place, is facilitated by the ammonia present in the synthesis solution and/or by ammonia fed for this purpose.

An advantage of the present disclosure therefore relates to an enhanced process for the preparation of urea from ammonia and carbon dioxide, at a high pressure and temperature, with the formation of ammonium carbamate as intermediate product, which includes a synthesis section comprising the following steps:

(i) reacting ammonia and carbon dioxide at an overall pressure ranging from 12 MPa to 20 MPa, with a molar ratio $NH_3/CO_2$, as such or in the form of ammonium carbamate, ranging from 2.1 to 6 (and specifically, in certain embodiments, from 2.8 to 4.5), in a reaction step carried out in a suitable vertical reactor R fed with at least one ammonia stream and at least one stream of fresh carbon dioxide containing a passivation agent in such a quantity that its equivalent oxygen content is at least 0.1% (and specifically, in certain embodiments, from 0.15% to 0.30%) in moles with respect to the moles of carbon dioxide, with the formation of a first liquid mixture containing urea, ammonium carbamate, water and ammonia, in liquid/vapour equilibrium with a gaseous phase containing at least a part of the passivation agent;

(ii) transferring said first liquid mixture to at least one decomposition-stripping step carried out in a suitable vertical apparatus, called stripper (S), operating at a pressure of at least 0.1 MPa (and specifically, in certain embodiments, from 0.2 MPa to 2.0 MPa, and more specifically, in certain embodiments, from 0.5 MPa to 1.5 MPa), lower than that of said reaction step (i);

(iii) heating said first liquid mixture in said decomposition-stripping step, to effect the decomposition of part of the ammonium carbamate into ammonia and carbon dioxide, and simultaneously subjecting said liquid mixture to stripping, such as using ammonia as stripping gas, with the formation of a first gaseous mixture containing ammonia and carbon dioxide, and a second liquid mixture containing urea, water, ammonia and the non-decomposed part of the ammonium carbamate;

(iv) transferring at least a part (and in one embodiment all), of said first gaseous mixture to at least one condensation step, substantially operating at the same pressure as the decomposition-stripping (iii) step and condensing the gaseous phase transferred with the formation of a third liquid mixture containing ammonium carbamate, water and ammonia;

(v) transferring said third liquid mixture and the possible remaining part of said first gaseous mixture to the reaction step (i);

characterized in that at least a part of said gaseous phase in equilibrium with the first liquid mixture of step (i), is separated in a gas-liquid separator (D1) situated downstream of the reactor (R) and substantially operating at the same pressure, to form a second gaseous mixture containing a passivation agent, which is fed to the lower section of said stripper (S).

A further advantage of the present disclosure relates to the section of a plant for the production of urea by direct synthesis from ammonia and carbon dioxide, suitable for effecting the above enhanced process.

In the present description, the term "heating or heated" referring to a liquid and/or gaseous stream or mixture, indicates that said stream or mixture has been subjected to a temperature rise.

According to the process of the present disclosure, which is normally carried out in continuous, in a suitable plant or section of a plant, fresh ammonia and carbon dioxide are continuously fed to the plant in order to balance the corresponding quantity of reagents used for the formation of urea, which is obtained at the outlet of the tail separation and purification section of the plant. Ammonia and carbon dioxide not converted to urea in the reaction section, are almost totally recovered in subsequent separation steps at decreasing pressure, and completely recycled to the reaction section. The process according to the disclosure is therefore of the so-called "total recycled" type.

All the equipment in contact with the corrosive mixtures containing ammonia, water, ammonium carbamate and carbon dioxide, as such or mixed with each other, generally consist of or are coated with corrosion-resistant metals or alloys according to normal construction standards of this type of plant, well-known to experts in the field. In particular, the metallic walls in contact with these corrosive mixtures such as mixtures made of titanium or zirconium or an alloy thereof, or one of the suitable stainless steels known to experts in the field, such as, for example, AISI316L steel (urea grade), 25/22/2 Cr/Ni/Mo stainless steel, special austenitic-ferritic steels, low-ferrite austenitic steels, etc. As previously mentioned, these materials, especially stainless steels, are particularly resistant to the corrosive action of salts such as ammonium carbamate at high pressures and temperatures, when it is possible to form and maintain on their surfaces a thin layer (normally having a thickness less than 1 micron) of stable oxide, and they therefore require the constant presence, during the process, of a suitable quantity of passivating agent (i.e., oxidant), which limits the degradation of the surface oxide and possibly restores its presence.

Fresh ammonia can be fed directly to the reaction step (i) but the fresh ammonia is, in one embodiment used, at least partially, as motor fluid in one or more ejectors, in order to provide the necessary thrust for transferring, according to step (v), said third liquid mixture containing the ammonium carbamate coming from the condensation step (iv). In the continuous plant for effecting the process of the present disclosure, the stream of fresh ammonia, normally mixed with a part of the recycled ammonia, is, in one embodiment, compressed at a pressure 2 MPa to 10 MPa higher than that of the reactor, and heated to a temperature ranging from 30° C. to 130° C. (and specifically, in certain embodiments, from 80° C. to 120° C.), according to what is known in the art, and is then fed to an ejector where the stream of fresh ammonia intercepts and entrains said third liquid mixture. Under the above pressure and temperature conditions, the ammonia, as such or mixed with water or ammonium carbamate, is normally in the liquid state.

Alternatively, or also contemporaneously with its use in the ejectors, the fresh ammonia can be partially sent (in one embodiment not exceeding 30% by weight) to the stripper as stripping fluid, in addition to that formed in situ by evaporation from the first liquid mixture, and/or directly sent to the condenser.

In the process according to the present disclosure, wherein, in the reaction step (i), an excess of ammonia is used with respect to the stoichiometric ratio with the carbon dioxide necessary for producing ammonium carbamate and, subsequently, urea (2/1 in moles), the stream leaving the reactor and, in general, most of the liquid streams formed in the process, normally contain an excess of ammonia. During the present description, reference is made to the composition of these liquid streams and mixtures, conventionally assuming that all the carbon dioxide is in the form of ammonium carbamate, and the remaining excess of ammonia is in the form of free ammonia or, more simply, ammonia.

According to the present disclosure, the fresh $CO_2$ is, in one embodiment, fed directly to the reactor, even if there are variants of the process in which up to 50% of the $CO_2$ can be fed to other process steps, such the condenser and one or more separation steps of the non-converted reagents.

The stream of fresh $CO_2$ fed to the reactor has a temperature which normally ranges from 100° C. to 200° C. (and specifically, in certain embodiments from 110° C. to 140° C.). In one embodiment, this temperature is reached with no external heat supplies, but exploiting the heat produced in the compression steps, according to the known techniques.

In accordance with the present disclosure, the fresh $CO_2$ sent to the reactor contains a passivating agent in such a quantity that its equivalent content of $O_2$ in moles is equal to at least 0.1%, (and specifically, in certain embodiment, from 0.15% to 0.30%) in moles with respect to the moles of carbon dioxide. Said passivating agent is normally an oxidant which can be selected from air, oxygen, ozone, air enriched with $O_2$, hydrogen peroxide or mixtures thereof, such as air or air enriched with oxygen. Said passivating agent is suitably added to the fresh feeding $CO_2$ before or during the first of the normal compression phases for bringing the gas to the operating pressure of the reactor.

When the passivating agent consists of air or enriched air, a certain quantity of inert gases (such as nitrogen, argon, etc.) are also introduced into the reactor and are added to those possibly present as impurities in the ammonia, such as methane or hydrogen. These gases, even if in relatively small quantities, can advantageously have a significant role in regulating the liquid/vapour equilibria and as additional entrainment fluids in evaporation and stripping operations.

The term "equivalent content of $O_2$", as used herein with reference to the passivating agent, defines the quantity of $O_2$ in moles which should be used instead of the passivating agent for obtaining the same conversion in a redox reaction. It corresponds to the moles of $O_2$ in the case of air and oxygen, and to half of the moles of $H_2O_2$ and $\frac{3}{2}$ of the ozone moles.

In one embodiment, the process according to the present disclosure comprises a synthesis phase of urea, in which the molar ratio ammonia/carbon dioxide in the reaction step ranges from 2.8 to 4.5 (and specifically, in certain embodiments, from 3.0 to 4.0). As is known, this ratio does not correspond to the molar ratio between $NH_3$ and $CO_2$ when they are fed fresh, which is about 2 (corresponding to the stoichiometric value according to the reaction (1)) in a typical total recycling process. The synthesis reactor normally operates at temperatures ranging from 150° C. to 215° C., (and specifically, in certain embodiments, from 160° C. to 195° C.), and at pressures ranging from 12 MPa to 20 MPa (and specifically, in certain embodiments, from 14 MPa to 18 MPa). The regulation of the temperature of the reactor to the desired value can be effected following one of the methods known in the art, for example, in addition to the mentioned heating of the ammonia and/or carbon dioxide stream in the feeding, by providing the reactor with a heating resistance, or by sending a part of the gases leaving the stripper directly to the reactor.

The vertical reactor normally comprises a cylindrical body which is divided, in its interior, into superimposed sectors which communicate using various plates, of a type selected from those known in the art, so as to obtain optimum plug flow conditions, also in the presence of biphasic systems.

The reactor can also comprise various reaction zones, suitably interconnected with each other, possibly having different feeding streams.

The reactor must have a liquid hold-up which is such as to enable a residence time in the same ranging from a few minutes to a few tens of minutes, in order to enable the ammonium carbamate, formed by the reaction of ammonia with carbon dioxide in the condensation step and/or in the same reactor, to dehydrate to urea until the equilibrium composition is reached.

The reaction mixture is collected from the upper section of the reactor, normally using an overflow (T) connected to a conduit which descends, at least in part, inside the reactor, so as not to require thick high-pressure containment walls, subsequently exiting from the reactor at a suitable height to be connected with the gas-liquid separator D1.

Under the above-mentioned conditions, ammonia, carbon dioxide and ammonium carbonate fed with the third liquid mixture, or formed in the reactor according to the reaction (1a), react with the formation of urea, whose conversion at equilibrium in any case does not exceed 80%, and is usually lower than 70%, of the theoretical yield with respect to $CO_2$. In the upper section of the reactor (R), a biphasic mixture is therefore formed, consisting of said first liquid mixture in equilibrium with a gaseous phase containing at least a part of the passivating agent. Depending on the pressure and temperature conditions of the reactor and composition of the biphasic mixture, it is possible to regulate, according to physico-chemical parameters well-known to experts in the field, the relative amount of gas and liquid present in equilibrium in the reactor, thus determining the most suitable quantity of gaseous phase available for being sent as second gaseous mixture to the subsequent separation and stripping step.

According to certain non-limiting aspects of the present disclosure, the biphasic mixture collected from the reactor using the overflow, comprises a quantity of gaseous phase not higher than 5% by weight (and specifically, in certain embodiments from 1 to 4% by weight), with respect to the weight of the liquid phase. According to a different aspect of the present disclosure, however, by operating in the reactor with a higher thermal level (temperature at the head ranging from 190° C. to 200° C.), a gaseous phase can be obtained also in a quantity of up to 10% by weight with respect to the weight of the liquid phase, particularly if the second gaseous phase sent to the bottom of the stripper (S) with the additional function of stripping agent in addition to that of passivation, is to be exploited.

The term "passivating agent" as used in the present description and claims refers to both the passivating agent introduced in step (i) with the stream of fresh carbon dioxide, and the oxidant/passivating products deriving from the same, such as, for example, oxygen deriving from the decomposition of ozone or a peroxide initially fed to the reactor.

A fundamental advantage of the enhanced process according to the present disclosure, is that it enables an optimization of the operativeness of the stripper, without resorting to additional pumpings of the passivating agent, and contemporaneously regulating its dosage at the bottom of the stripper.

Secondly, the present process enables the flow of passivating agent to the bottom of the stripper and the operative conditions of the separation step downstream the reactor, to be simply and effectively regulated, through the regulation of the pressure difference between the reaction step (i) and the decomposition and stripping step (iii). In certain embodiments, this is achieved with the combined use of two pressure-reduction valves (depressurization) situated downstream of the separator D1.

The present process also has the advantage of being easily and surprisingly effected by applying a few simple modifications to an existing traditional plant, provided it has a high-pressure stripping step. In particular, it is sufficient to modify the plant so as to send, to said stripping step, a gaseous stream separated from the effluent of the reactor and regulated, using a valve, at a pressure slightly below that of the latter.

A further advantage lies in the possibility of using strippers made of any urea-resistant steel material.

According to one embodiment of the present disclosure, said biphasic mixture leaving the reactor, such as through the overflow, is sent to a gas-liquid phase separator, where the gas phase is separated from the liquid and is fed as a second gaseous mixture to the lower part of the vertical stripper (S), whereas the remaining liquid mixture, forming said first liquid mixture, is fed to the head area of the same stripper.

Said second gaseous mixture (or stream) comprises at least a part of the passivating agent, such as from 60% to 100%, more specifically from 60% to 95% (normally oxygen in this step), the remaining part being dissolved in the first liquid mixture fed to the head of the stripper. Said second gaseous mixture, however, does not necessarily have the same composition as the gaseous phase present in the reactor, but the corresponding composition at equilibrium formed in the separator (D1).

In addition to the passivating agent, the second gaseous mixture comprises most of the inert gases, such as nitrogen, argon, and traces of methane or hydrogen, introduced into the process in various ways, for example with the passivation air or as impurities in the feeding gases. Additional quantities of inert gases can also be introduced as stripping gases. The second gaseous mixture also contains a prevalent part of gaseous ammonia, in addition to smaller quantities of $CO_2$, and possibly water vapour.

In certain embodiments, said second gaseous mixture collected from the separator D1 and fed to the lower section of the stripper (S) has a temperature ranging from 170° C. to 200° C. and forms a weight percentage not higher than 5% (and specifically, in certain embodiments, from 1% to 4%) by weight, with respect to the weight of the first liquid mixture fed to the upper section of the stripper.

The gas-liquid separator (D1) is of the type normally used in the art for this purpose and comprises a simple hollow cylindrical body having relatively small dimensions, sufficient for enabling the demixing of the phases. The biphasic mixture coming from the reactor is fed at an intermediate height which can be indifferently either above or below the level of the liquid, which is suitably regulated using the valve (V2) positioned on the liquid stream, downstream of the separator. The gaseous mixture is collected from the head area and the liquid mixture from the bottom area.

According to the present disclosure, in order to be transferred to said decomposition-stripping step (iii), both said first liquid mixture and said second gaseous mixture are depressurized to the operating pressure of the stripper (S), which differs from that of the reaction step according to what is specified above in accordance with step (ii). This is suitably achieved through the passage of each of the above mixtures (or streams) through a pressure-reducing device, such as a valve.

In particular, the pressure and flow-rate of said second gaseous mixture fed to the lower section (bottom section) of the stripper are regulated using a first valve (V1), and consequently the pressure difference between the reactor and the stripper.

The flow-rate of the first liquid stream, and consequently the liquid level in the separator (D1), on the other hand, is regulated using a second valve (V2).

An expert in the field can suitably control and regulate the amount of gaseous mixture fed to the bottom of the stripper, by the combined use of the two above-mentioned valves, thus optimizing the running of the decomposition-stripping step (iii). Valves suitable for this function, such as, for example, butterfly valves, suitably produced and dimensioned in relation to the flows, the operating pressures and nature of the fluids involved, are commercially available and can be found by experts in the field.

In accordance with the present disclosure, the decomposition-stripping step (iii) is suitably carried out in a vertical stripper (S) normally heated using indirect high-pressure vapour. In certain embodiments, the stripper (S) comprises a distribution chamber at the head, positioned in the upper area, to which said first liquid mixture is fed, and a collection chamber positioned in the lower area, to which said second gaseous stream is fed, interspaced by a tube bundle, in a vertical position when in use, so that the liquid mixture to be treated forms by falling, an almost uniform liquid film along the walls of the tubes. The distribution chamber is generally situated in the 20% upper section of the stripper and the collection chamber in 20% lower one.

The temperature of the stripper normally ranges from 170° C. to 210° C. (and specifically, in certain embodiments, from 180° C. to 200° C.) in the upper section, also called head, whereas the temperature of the stripper ranges from 180° C. to 220° C. (and specifically, in certain embodiments, from 190° C. to 210° C.) in the lower section, also called tail. In certain embodiments, the pressure is from 0.2 MPa to 2.0 MPa (and specifically, in certain embodiments, from 0.5 MPa to 1.5 MPa) lower than that of the reactor.

Under the above conditions, the ammonium carbamate tends to rapidly decompose forming ammonia and carbon dioxide, whereas the urea already formed in the reactor remains substantially unchanged. The stripping is carried out using ammonia as stripping gas. In one embodiment of the present disclosure, the decomposition-stripping step is effected using, as stripping gas, the same ammonia present in excess in the stream leaving the reactor. Further details on this technology can be found, for example, in U.S. Pat. No. 3,876,696, whose content is enclosed herewith as reference. This latter technology is called "self-stripping".

The first gaseous mixture formed in the decomposition-stripping step and fed, at least partially, to the condensation step (iv) comprises ammonia in excess, in addition to the $CO_2$ deriving from the decomposition of most of the ammonium carbamate not converted in the reactor and optionally, a small amount of water. The first gaseous mixture also contains the possible inert gases and passivating agent contained in the feeding streams of the stripper. According to one embodiment of the present disclosure, the whole of the first gaseous mixture is transferred to the condensation step, however, when necessary, an expert in the field can decide to transfer a part, not exceeding 20%, of said gaseous mixture with a high thermal content, directly to the reactor, in order to regulate its energy balance.

The condensation step (iv) is normally carried out in appropriate condensers, for example of the tube-bundle or surface type, in which the condensation heat is used for heating other fluids. In certain embodiments, the condensation heat is used for producing vapour, but can also be used, according to certain variants known in the art, for providing heat to one of the subsequent decomposition steps of ammonium carbamate at medium or low pressure.

The condensation step (iv) can be carried out under the usual conditions (temperature, pressure and composition) adopted in the known processes, provided these are such as to prevent the formation of solid ammonium carbamate in the condenser and/or in the lines leaving the same. The pressure of the condenser (C) is substantially the same as that of the stripper (S) or 100 KPa to 200 KPa lower.

The third liquid mixture formed in the condensation step is transferred to the reactor (R) and substantially forms the recycling of the reagents not converted into urea. As the reaction step (i) is carried out at a higher pressure than that of step (iv), the transferring of the third liquid mixture to the reactor in accordance with step (v) of the process of the present disclosure suitably comprises a recompression phase. This can be carried out by pumping, but it has been found to be more convenient, due to the pressure differences involved, to use the thrust of an ejector fed by a stream at a high pressure of pure ammonia, comprising the fresh ammonia in the feed, and possibly a stream of liquid ammonia coming from the urea purification sections.

The inert products and passivating oxygen transferred to the condensation step with the first gaseous mixture are not condensable and remain as gaseous phase, which can be removed directly from the condenser (C), but are, in certain embodiments, separated in a second separator (D2) situated downstream of the condenser. The stream of inert and passivating products thus obtained, which generally also contains ammonia and/or $CO_2$ in relation to the liquid-vapour equilibrium with respect to the third liquid mixture, can be purged from the plant or is conveniently sent to the subsequent urea separation and purification sections, where the passivating agent can still contribute to maintaining an effective corrosion-resistance of the materials exposed.

The separation and purification of urea from the ammonia and ammonium carbamate still present in the second liquid mixture produced in the decomposition-stripping step (iii), are effected in subsequent decomposition and separation sections, operating at medium pressure (from 1.1 MPa to 2.5 MPa) and/or low pressure (from 0.2 MPa to 0.8 MPa). This separation step can be effected using any of the methods described in specific literature in the field, which enable a recycled liquid stream containing an aqueous solution of ammonium carbamate and ammonia to be obtained, and possibly, also a stream essentially consisting of ammonia.

Suitable separation and purification sections, for example, are those schematically represented in FIGS. 1 to 5 of the publication "Encyclopaedia of Chemical Technology" previously mentioned.

The urea thus separated from the ammonium carbamate and ammonia, is generally obtained as an aqueous solution which is subjected to a final dehydration step under vacuum (up to 0.001 MPa), obtaining, on the one hand, water and, on the other, substantially pure urea, sent to normal prilling processes, etc.

The separation and purification step of urea also comprises the final dehydration step and purification section of the wastewater leaving the synthesis plant.

The various liquid or biphasic streams containing ammonium carbamate, coming from the different subsections of the separation and purification step (decomposition of the carbamate at medium and low pressure, recondensation of the carbamate, dehydration of urea, purification of the wastewater) are collected in a single recycled stream, generally consisting of an aqueous solution of ammonium carbamate, which is sent, after suitable compression, normally using a pump, to the high-pressure condenser where the above-mentioned condensation step (iv) takes place. The pump used for this purpose, is selected, on the basis of the required flow-rates, from those normally available on the market, such as, for example, reciprocating pumps, centrifuges or dosers. The recycled liquid mixture favours the high-pressure condensation of step (iv) and is then recycled to the reactor as part of said third liquid mixture.

Figure 1:
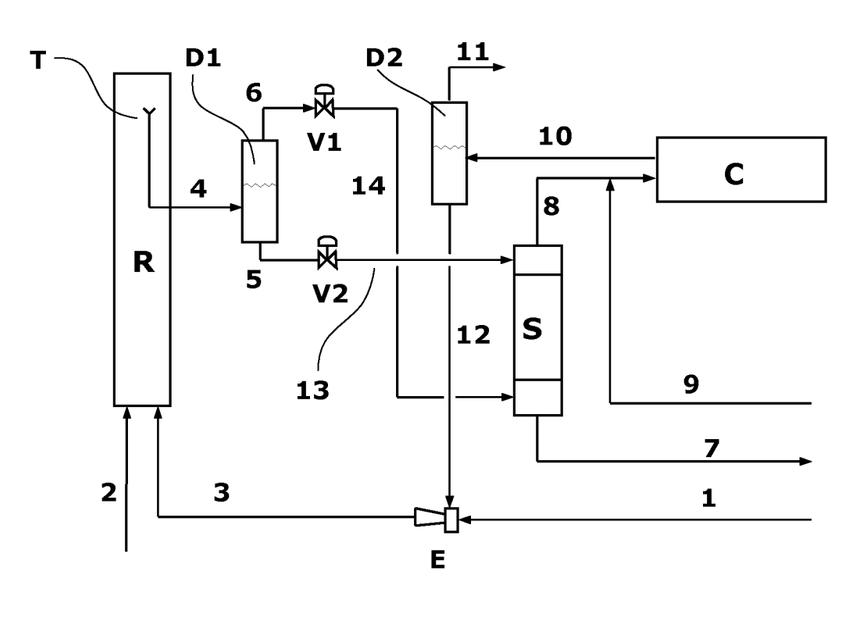
FIG. 1 shows a schematic view of one embodiment of a high-pressure and temperature synthesis section of urea.

The process according to the present disclosure is further illustrated according to the scheme represented in FIG. 1, relating to one embodiment of the high-pressure and temperature synthesis section of urea.

Parts and possible equipment such as pumps, valves, sensors et al, which are not significant for a full understanding of the schematized process, are not shown in the above FIG. 1. In no case should the process according to the present disclosure be considered as being limited to what is described in the enclosed FIGURE, which has a purely illustrative purpose.

The scheme of FIG. 1 illustrates the reactor (R) which is connected, through the overflow (T) and line 4, with the gas/liquid separator (D1), in turn connected from its lower section, normally from the bottom, to the stripper (S) through lines 5 and 13 for conveying the liquid mixture of the reaction products, interposed by the depressurization valve (V2). The gaseous phase separated (second gaseous stream) is transferred from the upper section (head) of the same separator (D1) to the bottom section of the stripper (S) through lines 6 and 14, interposed by the depressurization valve (V1). Said stripper (S) is connected from below, through line 7, with the urea separation and purification section (not shown in the FIGURE), from which, through line 9, the solution of ammonium carbamate is recycled to the condenser (C), possibly together with a stream of liquid ammonia, almost pure, which is added to the feeding stream of fresh ammonia, sent to the ejector (E) through line 1. The outlet of the gases from the stripper (S) is connected to the condenser (C) through line 8. The outlet of the condenser (C) is represented by line 10 which is then connected to the separator (D2) from whose top the inert gases are removed together with the purging gas through line 11, and from whose bottom, line 12 exits, which carries the feeding stream of recycled product (third liquid mixture) to the reactor (R) through the ejector (E) and feeding line 3.

The process according to the present disclosure can be carried out in a plant having the above characteristics, equipped with a synthesis section comprising the equipment and connections indicated above with reference to the scheme of FIG. 1.

A further advantage of the present disclosure therefore relates to a plant configured to effect the process according to the present disclosure, comprising a synthesis section in which a vertical reactor (R) is in fluid connection with a vertical stripper (S) of the falling liquid film tube-bundle type, characterized in that a gas-liquid separator (D1) is interposed between said reactor and said stripper, said separator being connected at one side to the head of the reactor (R), from which two fluid connection lines are generated with said stripper (S), so that a transport line of a gaseous mixture connects the head of said separator (D1) with the lower section of the stripper (S) and a transport line of a liquid mixture connects the bottom of said separator (D1) with the upper section of the stripper (S). In certain embodiments, between said separator (D1) and said stripper (S), two pressure-reduction devices, such as two valves (V1) and (V2) are also interposed, each respectively on one of the two fluid connection lines of said equipment.

This plant can be obtained as such starting from a new construction, or it can be simply and conveniently obtained by modifying an existing plant for the synthesis of urea, equipped with a stripper suitable for operating under self-stripping conditions, with the use of a gas-liquid separator (D1) downstream of the reactor (R), connected to the stripper (S) by use of two lines, so that a head line configured to convey a gaseous mixture is connected to the lower section of the stripper through a first pressure-reduction device, such as a valve (V1) and a bottom line configured to convey a (first) liquid mixture is connected to the upper section of the stripper through a second pressure-reduction device, such as a valve (V2).

A further advantage of the present disclosure therefore relates to a method for enhancing an existing process for the production of urea starting from ammonia and carbon dioxide with the intermediate formation of ammonium carbamate which operates with a high-pressure synthesis section, comprising:

a reaction step carried out in a vertical reactor (R) fed with at least a stream of fresh carbon dioxide and at least a liquid ammonia stream, operating at an overall pressure ranging from 12 MPa to 20 MPa, with a $NH_3/CO_2$ molar ratio, as such or in the form of ammonium carbamate, ranging from 2.1 to 6 (and specifically, in certain embodiments, from 2.8 to 4.5), with the formation of an outgoing liquid mixture in the upper zone of the reactor, containing urea, water, ammonia and non-converted ammonium carbamate;

a decomposition-stripping step of the ammonium carbamate in said liquid mixture with the separation of a gaseous stream containing carbon dioxide and the ammonia thus formed, carried out in a suitable vertical tube-bundle apparatus called stripper (S) situated downstream of said reactor (R); and a condensation step in a condenser (C) of the gaseous stream leaving said stripper (S), with the formation of a liquid stream containing ammonium carbamate, fed as recycled product, to said first reactor, characterized in that the method comprises the following operations:

(a) introducing a passivation agent into said carbon dioxide stream fed to the reactor, such as before the compression phase to the pressure of the reactor, in such an amount that its equivalent oxygen content is at least 0.1% (and specifically, in certain embodiments, from 0.15% to 0.30%) in moles, with respect to the moles of carbon dioxide, (b) regulating the pressure and temperature conditions of the reactor so that a gaseous phase is formed at least in the upper zone of the same, containing at least a part of the passivation agent in liquid-vapour equilibrium with said liquid mixture;

(c) positioning a gas-liquid separator (D1) between said reactor (R) and said stripper (S), substantially operating at the same pressure as the reactor, to form a second gaseous mixture containing at least a part of the passivation agent, which is fed into the lower section of said stripper (S), the remaining liquid mixture being fed into the upper section of the same stripper;

(d) establishing the operative conditions of said decomposition-stripping step in the stripper (S) so that said decomposition-stripping step is carried out at a pressure of at least 0.1 MPa (and specifically, in certain embodiments, from 0.2 MPa to 2.0 MPa, and more specifically, in certain embodiments, from 0.5 MPa to 1.5 MPa) lower than that of said reaction step.

In one embodiment of said enhancement method (or revamping, according to the more widely-used English term), two pressure-reduction devices are interposed between said separator (D1) and said stripper (S), such as two valves of the type (V1) and (V2) described above, acting on the feeding streams to the stripper, respectively consisting of said second gaseous mixture and said liquid mixture.

With reference to FIG. 1, some embodiments of the process of the present disclosure are now described, said description in no way limiting the overall scope of the disclosure.

In the following example, the compositions of the various streams are provided, making reference to the basic components, urea, ammonia, carbon dioxide, and water, regardless of the fact that carbon dioxide and ammonia can be present, in the liquid streams, in one of the saline forms previously indicated. Air and inert products are indifferently indicated with the term "air", as the oxygen consumption under regime conditions in the synthesis cycle is almost negligible.

Example

A process was effected for the synthesis of urea, which operates according to the present disclosure, on the basis of the scheme shown in FIG. 1, in which a gaseous stream containing $CO_2$, $NH_3$ and a suitable amount of $O_2$ as passivating agent, was fed to the base of the stripper (S), in addition to inert products and traces of water, coming from the gas-liquid separation unit (D1). No further quantity of air or other passivating agent was fed separately to the bottom of the stripper or to other parts of the plant. Reference is made to the scheme shown in FIG. 1 and to a nominal production of 1,000 kg/h of urea. The impurities present with flow-rates lower than 0.5 kg/h, such as, for example, hydrogen, helium, biuret, metal salts, are ignored.

The following products were fed respectively to the reactor (R):
- 730 kg/h of $CO_2$ and 8 kg/h of air through line 2, as gaseous stream at 120° C. and 16.3 MPa;
- 492 kg/h of $CO_2$, 1,700 kg/h of $NH_3$ and 300 kg/h of water through line 3, as a solution of ammonium carbamate at 130° C. and 16.3 MPa, obtained from the combination, through the ejector (E), of 790 kg/h of substantially pure liquid $NH_3$ through line 1 with the recycled solution of ammonium carbamate through line 12, containing 492 kg/h of $CO_2$, 910 kg/h of $NH_3$ and 300 kg/h of water.

The term air refers in the present example to a mixture of gases corresponding to the average composition of dry air at sea level, essentially containing 75.4% by weight of nitrogen, 23.2% by weight of oxygen, 1.4% by weight of argon, the other gases being in a negligible quantity. Air is introduced in the first step of the fresh $CO_2$ compressor (not shown in the FIGURE).

The reactor (R), substantially adiabatic and of the traditional type, reaches a pressure in the area of the head, of about 16.0 MPa and a temperature of the reaction mixture of 190° C. Under these conditions, the reaction mixture is in the liquid state for about 97% by weight.

The biphasic stream 4, discharged from the overflow (T) of the reactor (R) at substantially the same pressure and temperature, containing all of the urea produced, was sent to the gas-liquid separator (D1). In particular, the bisphasic stream 4 is characterized by the following composition:
- Urea=1000 kg/h
- $H_2O$=600 kg/h
- $CO_2$=489 kg/h
- $NH_3$=1133 kg/h
- Air=8 kg/h The separator (D1) substantially operates at the same pressure and temperature as the head of the reactor (R). The separator comprises a vertical cylindrical body equipped with automatic detection of the liquid level.

A liquid stream (first liquid mixture) is collected from the bottom of the separator (D1) through line 5, having the following composition:
- Urea=1000 kg/h
- $H_2O$=600 kg/h
- $CO_2$=487 kg/h
- $NH_3$=1083 kg/h
- Air=1 kg/h Said stream is brought to a pressure of 15.1 MPa and a temperature of 188° C. through the valve (V2) consisting of an automatic control valve of the butterfly type, activated in relation to the level detector in the separator (D1), and is then fed to the head of the stripper (S) through line 13.

A gaseous stream (second gaseous mixture) consisting of 2 kg/h of $CO_2$, 50 kg/h of $NH_3$ and 7 kg/h of air, is collected from the head of the separator (D1), through line 6. Said gaseous mixture is expanded through the valve (V1) to a pressure of 15.1 MPa and a temperature of 188° C., and fed to the lower section of the stripper (S) through line 14, such as at a height above the level of the liquid in the bottom of the stripper.

The gaseous mixture fed to the bottom of the stripper contains most of the passivating oxygen introduced into the reactor and substantially all of the inert gases. In this way the gaseous mixture can be optimally distributed in the collection chamber of the stripper bottom and can exert a double stripping and passivation action starting from the metallic walls exposed to the most extreme corrosion conditions, as the temperature is at its highest (higher than 200° C. in industrial plants currently in use).

The stripper (S) operates at 15.1 MPa and a temperature at the bottom of 207° C., under self-stripping conditions. The equipment consists of a conventional vertical tube-bundle stripper having a suitable volume with tubes and internal coating in 25/22/2 Cr/Ni/Mo stainless steel for use in the synthesis section of urea, whose structure and construction characteristics are well-known to experts in the field and widely described in specific technical literature.

A gaseous stream (first gaseous mixture) is discharged from the head of the stripper (S), at 190° C. and 15.1 MPa, and fed to the condenser (C) through line 8, characterized by the following composition:
- $CO_2$=374 kg/h
- $NH_3$=618 kg/h
- $H_2O$=102 kg/h
- Air=8 kg/h A liquid stream 7 was discharged from the bottom of the stripper (S), consisting of:
- Urea=1000 kg/h
- $H_2O$=498 kg/h
- $CO_2$=115 kg/h
- $NH_3$=515 kg/h which is sent to the subsequent urea purification and concentration steps, (not shown in the FIGURE for the sake of simplicity). These substantially consist of typical medium pressure and low pressure separation sections, and the concentration section of the tradition SNAMPROGETTI Urea Process whose general scheme is provided, for example, on page 561 of the publication "Encyclopaedia of Chemical Technology", previously mentioned. An aqueous stream rich in carbamate, having a temperature of about 100° C., consisting in particular of:
- $H_2O$=198 kg/h $CO_2$=121 kg/h
$NH_3$=342 kg/h was recovered from said purification and concentration section downstream of the stripper (S), and was recompressed at a pressure of 15 MPa using a pump and sent to the condenser (C) through line 9, after being joined with the gaseous stream 8 leaving the stripper (S).

A liquid stream 1 of 790 kg/h of ammonia, also comprising fresh feeding ammonia, is recovered from the same section, which is compressed at 22.4 MPa and sent, at a temperature of 100° C., to the ejector (E), where, thanks to the high pressure, it causes the thrust of the stream 12 of recycled ammonium carbamate which is thus brought back to the operating pressure of the reactor (R).

A biphasic mixture consisting of the combination of streams coming from the above lines 8 and 9 is fed, tube side, to the condenser (C), of the horizontal tube-bundle exchanger type (known to experts as Kettle-type condenser). Most of the $CO_2$ still gaseous condenses in the condenser (C), which operates at 15 MPa and about 155° C., and reacts to form ammonium carbamate, whereas the heat produced is subtracted by exchange with the formation of medium-pressure vapour (about 1 MPa).

The stream 10, prevalently liquid, leaving the condenser (C), having the following composition:
$H_2O$=300 kg/h
$CO_2$=495 kg/h
$NH_3$=960 kg/h
Air=8 kg/h is sent to the gas/liquid separator (D2), from which a gaseous stream 11 consisting of $CO_2$=3 kg/h; $NH_3$=50 kg/h; air=8 kg/h, is obtained at the head, and the remaining stream 12 at the bottom, recycled to the reactor (R) using the ejector (E), as previously specified.

Under the process conditions indicated above, and with the plant started and under regime conditions, the oxygen consumption is virtually null and all the oxygen is practically recovered together with the other inert products, from the stream of line 11, subsequently sent to the urea purification steps from which, finally, a stream having the composition substantially similar to that of the air fed as passivating agent to the reactor (R), is purged in the open-air.

A synthesis process of urea effected according to the above example for a running period of a year did not show any significant corrosion phenomena, either at the bottom of the stripper or in the other parts and sections of the plant, even in the absence of a separate feeding of the passivating agent to the stripper.

Clearly, changes may be made to the embodiment described of the present disclosure without, however, departing from the protective scope of the accompanying Claims. That is, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A urea preparation process comprising:
   (a) reacting, in a vertical reactor and at an overall pressure ranging from 12 MPa to 20 MPa, at least one ammonia stream and at least one fresh carbon dioxide stream having an ammonia to carbon dioxide molar ratio ranging from 2.1 to 6, the at least one carbon dioxide stream containing a passivation agent having an oxygen content of at least 0.1% in moles with respect to the moles of carbon dioxide, the reaction forming a first liquid mixture containing urea, ammonium carbamate, water and ammonia in a liquid/vapour equilibrium with a gaseous phase containing at least a part of the passivation agent,
   (b) transferring the first liquid mixture to a vertical stripper operating at a pressure of at least 0.1 MPa lower than that of the reaction;
   (c) separating at least a part of the gaseous phase in the liquid/vapour equilibrium with the first liquid mixture in a gas-liquid separator situated downstream of the reactor, the gas-liquid separator operating at substantially the same overall pressure to form a first gaseous mixture containing the passivation agent,
   (d) feeding the first gaseous mixture containing the passivation agent to a lower section of the stripper,
   (e) simultaneously:
      (i) heating the first liquid mixture to decompose part of the ammonium carbamate into ammonia and carbon dioxide, and
      (ii) stripping the liquid mixture to form:
         (A) a second gaseous mixture containing ammonia and carbon dioxide, and
         (B) a second liquid mixture containing urea, water, ammonia and any non-decomposed part of the ammonium carbamate;
   (f) condensing, at a same pressure as the heating and stripping, at least a part of the second gaseous mixture to form a third liquid mixture containing ammonium carbamate, water and ammonia; and
   (g) transferring the formed third liquid mixture and any remaining part of the second gaseous mixture to the reactor for at least one repeat of at least (a).

2. The urea preparation process of claim 1, wherein the ammonia to carbon dioxide molar ratio ranges from 2.8 to 4.5.

3. The urea preparation process of claim 1, wherein the passivation agent has an oxygen content from 0.15 to 0.30% in moles with respect to the moles of carbon dioxide.

4. The urea preparation process of claim 1, which includes operating the stripper at a pressure of 0.2 to 2.0 MPa lower than that of the reaction.

5. The urea preparation process of claim 1, which includes transferring all of the second gaseous mixture to the at least one condensation step.

6. The urea preparation process of claim 1, wherein the stripping operates at a pressure ranging from 0.5 MPa to 1.5 MPa lower than that of the reaction.

7. The urea preparation process of claim 1, which includes stripping the second liquid mixture using ammonia as a stripping gas.

8. The urea preparation process of claim 7, which includes carrying out the decomposition and stripping of the ammonium carbamate with ammonia under self-stripping conditions.

9. The urea preparation process of claim 1, wherein the passivation agent is selected from the group consisting of: air, oxygen, ozone, air enriched with oxygen, hydrogen peroxide and a mixture of at least two of air, oxygen, ozone, air enriched with oxygen, hydrogen peroxide.

10. The urea preparation process of claim 1, wherein the reactor operates at temperatures ranging from 150° C. to 215° C.

11. The urea preparation process of claim 1, wherein the amount of the first gaseous mixture is not greater than 5% by weight with respect to the weight of the second liquid mixture.

12. The urea preparation process of claim 1, wherein the temperature of the stripper ranges, in an upper section, from 170° C. to 210° C., and the temperature of the stripper ranges, in the lower section, from 180° C. to 220° C.

13. The urea preparation process of claim 1, which includes depressuring both the first liquid mixture and the first gaseous mixture to a pressure of the stripping by passing each of the first liquid mixture and the first gaseous mixture through a pressure reducer device.

14. The urea preparation process of claim 13, which includes regulating, using a first valve, a flow-rate of the first gaseous mixture and a pressure difference between the reactor and the stripper.

15. The urea preparation process of claim 13, which includes regulating, using a second valve, a flow-rate of the first liquid stream from the gas-liquid separator to the stripper to regulate a level of liquid in the gas-liquid separator.

* * * * *